US00PP25475P2

(12) United States Plant Patent
Hachmann

(10) Patent No.: US PP25,475 P2
(45) Date of Patent: Apr. 28, 2015

(54) *ILEX* PLANT NAMED 'HACH 1'

(50) Latin Name: *Ilex×meserveae*
Varietal Denomination: Hach 1

(71) Applicant: Holger Hachmann, Barmstedt (DE)

(72) Inventor: Holger Hachmann, Barmstedt (DE)

(73) Assignee: Hachmann Baumschulen, Barmstedt (DE)

( * ) Notice: Subject to any disclaimer, the term of this patent is extended or adjusted under 35 U.S.C. 154(b) by 169 days.

(21) Appl. No.: 13/986,840

(22) Filed: Jun. 10, 2013

(51) Int. Cl.
*A01H 5/00* (2006.01)

(52) U.S. Cl.
USPC ..... Plt./247

(58) Field of Classification Search
USPC ..... Plt./247
See application file for complete search history.

*Primary Examiner* — Susan McCormick Ewoldt
(74) *Attorney, Agent, or Firm* — Penny J. Aguirre

(57) ABSTRACT

A new cultivar of *Ilex×meserveae*, 'Hach 1', characterized by upright, erect and narrow plant habit, its foliage that is greyed purple to brown in color in winter, and its lack of fruit production (male selection).

2 Drawing Sheets

Botanical classification: *Ilex×meserveae.*
Variety denomination: 'Hach 1'.

BACKGROUND OF THE INVENTION

The present invention relates to a new and distinct cultivar of *Ilex×meserveae* and will be referred to hereafter by its cultivar name, 'Hach 1'. 'Hach 1' is a new cultivar of blue holly grown for use as a landscape plant.

The new cultivar arose from a cross made by the Inventor in Barmstedt, Germany in spring of 1999 between 'Heckenpracht' (not patented) as the female parent and 'Blue Prince' (U.S. Plant Pat. No. 3,517) as the male parent. The Inventor selected 'Hach 1' as a single unique plant amongst the seedlings that resulted from the above cross in spring of 2002.

Asexual propagation of the new cultivar was first accomplished by the Inventor using softwood stem cuttings in summer of 2002 in Barmstedt, Germany. Asexual propagation by softwood stem cuttings has determined that the characteristics of the new cultivar are stable and are reproduced true to type in successive generations.

SUMMARY OF THE INVENTION

The following traits have been observed repeatedly and represent the characteristics of the new cultivar. These attributes in combination distinguish 'Hach 1' as a unique cultivar of *Ilex.*

1. 'Hach 1' exhibits an upright, erect and narrow plant habit.
2. 'Hach 1' exhibits new foliage growth that is greyed orange in color.
3. 'Hach 1' exhibits foliage that is greyed purple to brown in color in winter.
4. 'Hach 1' is a male selection and does not produce fruit.

The female parent, 'Heckenpracht', differs from 'Hach 1' in producing berries and in having a broadly pyramidal plant habit. The male parent, 'Blue Prince', differs from 'Hach 1' in producing winter foliage that is dark purple-green and in having an upright spreading plant habit. 'Hach 1' can be most closely compared to the cultivar 'Blue Angel' (not patented).

'Blue Angel' is similar to 'Hach 1' in summer foliage coloration. 'Blue Angel' differs from 'Hach 1' in producing fruit (female cultivar), in having a spreading upright plant habit, and in having winter foliage that is dark purple-green in color.

BRIEF DESCRIPTION OF THE DRAWINGS

The accompanying colored photographs illustrate the overall appearance and distinct characteristics of two-year-old plants of the new cultivar grown outdoors in 2-liter containers in Zevenaar, The Netherlands.

The photograph in FIG. 1 illustrates the upright and erect plant habit of 'Hach 1'.

Figure 1:
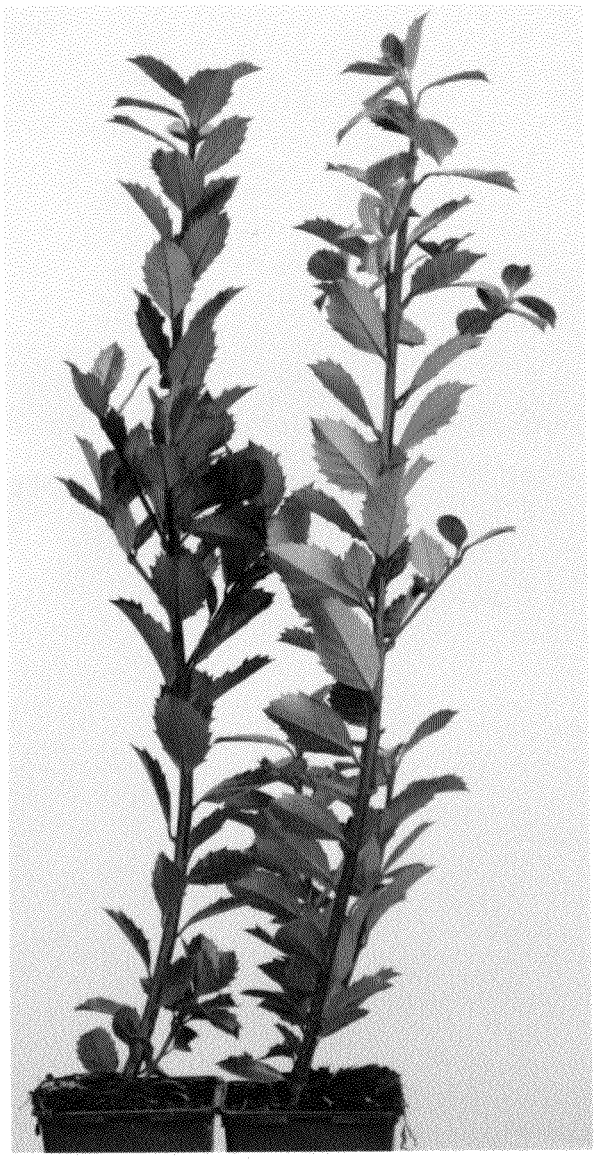
Figure 2:
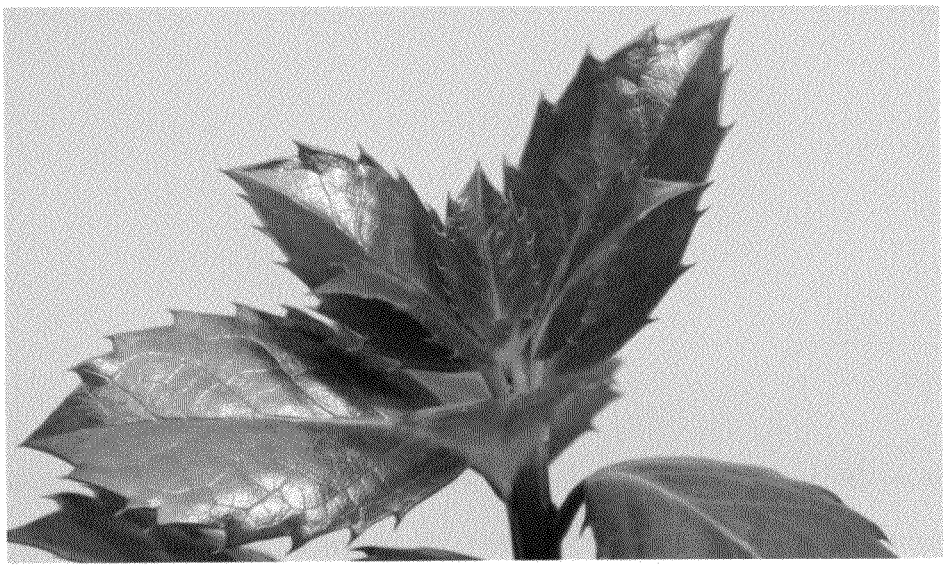

The photograph in FIG. 2 provides a close-up view of the new foliage of 'Hach 1'.

Figure 3:
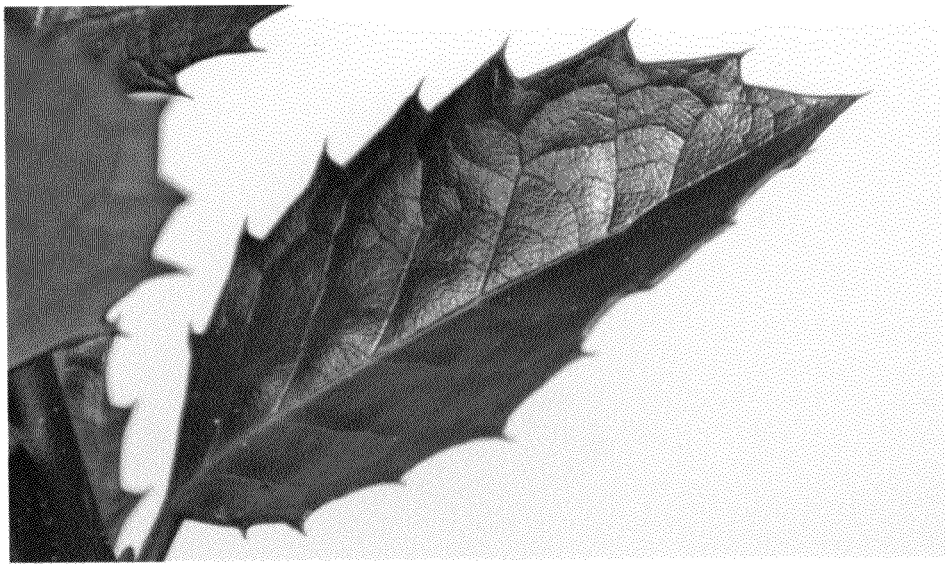

The photograph in FIG. 3 provides a close-up view of the mature foliage of 'Hach 1'.

The colors in the photograph may differ slightly from the color values cited in the detailed botanical description, which accurately describe the colors of the new *Ilex.*

DETAILED BOTANICAL DESCRIPTION

The following is a detailed description of one-year-old plants of the new cultivar grown outdoors in 2-liter containers in Zevenaar, The Netherlands. Plants were grown under average day temperatures of 10° to 20° C. and average night temperatures of 1° to 14° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Plant type.*—Evergreen shrub.

*Plant habit.*—Upright, erect, narrow plant habit.

*Height and spread.*—Reaches about 56.2 cm in height and 26.4 cm in spread on a one year-old plant.

*Cold hardiness.*—At least in U.S.D.A Zone 5.

*Diseases resistance*.—No susceptibility or resistance to diseases has been observed.

*Root description*.—Fine and slightly fibrous.

*Propagation*.—Softwood stem cuttings.

*Growth rate*.—Moderate.

Stem description:

*Shapes*.—Five-sided.

*Stem color*.—Young stem; N186C, mature wood; 200A.

*Stem size*.—Lateral branches are 12 cm in length and 4 mm in width.

*Stem surface*.—Smooth and dull, mature stems moderately covered with lenticels, average 1 mm in length and width, 195A to 195B in color.

*Internode length*.—Lateral branches; an average of 1.3 cm.

*Branching*.—Free branching, average of 7 lateral branches.

Foliage description:

*Leaf shape*.—Ovate to elliptic, moderately carinate.

*Leaf division*.—Simple.

*Leaf base*.—Attenuate.

*Leaf apex*.—Sharply pointed apiculate to acuminate, slightly curved downward.

*Leaf fragrance*.—None.

*Leaf venation*.—Pinnate, upper vein is 183D in color, lower vein is 187A in color.

*Leaf margins*.—Spinose, average of 14 spines per leaf (7 on each side).

*Leaf arrangement*.—Alternate.

*Leaf aspect*.—Held slightly upwards.

*Leaf attachment*.—Petiolate.

*Leaf surface*.—Glabrous, and moderately thick and leathery on both surfaces, very glossy on upper surface, slightly glossy on lower surface.

*Leaf size*.—Average of 5.2 cm in length and 3 cm in width.

*Leaf quantity*.—Numerous, average of 11 per branch.

*Leaf color*.—Young upper surface; 166A, young lower surface; color between 166A and 177A, mature upper surface; color between N137A and 147A, spines 185A, mature lower surface; color between 144A and 146B, edges are N186C, spines are 185A, winter color upper and lower surface; a color between 187A and 200A.

*Petioles*.—An average of 7 mm in length and 2 mm in width, N186C in color, glabrous surface.

*Spines*.—Slightly sharp, average of 1.5 mm in length and 185A in color.

Flower description:

*Inflorescence type*.—Axillary compound cyme.

*Inflorescence size*.—5 mm in height and 7 mm in width.

*Blooming period*.—Present for about 3 weeks in early spring.

*Flower type*.—Single, rotate.

*Number of flowers*.—9 per inflorescence, 90 per lateral stem, about 600 per plant.

*Fragrance*.—Faint, sweet.

*Flower buds*.—An average of 2 mm in length and 1.75 mm in diameter, color; 184B and 155B to 155D at base with calyx portion 176B to 176C.

*Flower size*.—An average of 3 mm in length and 6 mm in diameter.

*Flower longevity*.—About 3 days, self cleaning.

*Petals*.—Average of 4, arrangement cruciform, average of 2.5 mm in length and width, broadly elliptic to orbicular in shape, enitre margin, fused at base, rounded apex, color when flowers are opening and fully open, upper surface; 184C to 184D with base 155D, color when flowers are opening and fully open, lower surface; 184A to 184B with base 155D, non-fading, surface glabrous and dull on both surfaces.

*Sepals*.—Average of 4, fused in companulate shaped calyx (3 mm in diameter and 1.5 mm in length) with tips free and triangular in shape, enitre margin, broadly acute apex, base fused, 1.5 mm in length and width, color when flowers are opening upper and lower surface; 176B to 176C, surface glabrous on both surfaces.

*Peduncles*.—About 1 mm in length and width, held at an angle of about 30° from lateral branch axis, strong, smooth and glabrous surface, color a blend of 175A and 176A.

*Pedicels*.—About 1 mm in length and width, held in all directions of cyme, moderately strong, smooth and glabrous surface, color 155A and 157D.

*Reproductive organs*.—Androecium: about four, filament; about 3 mm in length and in about N155A in color, anther; reniform in shape, dorsifixed, about 1.5 mm in length, and 4D in color, pollen moderate in quantity and 8B in color, gynoecium: no female reproductive structures observed.

*Fruit*.—Male selection, no fruit is produced.

It is claimed:

1. A new and distinct cultivar of *Ilex* plant named 'Hach 1' as herein illustrated and described.

* * * * *